(12) United States Patent
Rousseau

(10) Patent No.: US 6,616,685 B2
(45) Date of Patent: Sep. 9, 2003

(54) HERNIA REPAIR DEVICE

(75) Inventor: Robert A. Rousseau, Ottsville, PA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/875,455

(22) Filed: Jun. 6, 2001

(65) Prior Publication Data

US 2002/0188317 A1 Dec. 12, 2002

(51) Int. Cl.$^7$ ............................................. A61B 17/08
(52) U.S. Cl. ........................ 606/213; 606/151; 623/11
(58) Field of Search .............................. 606/213, 215, 606/151, 200, 1, 62, 63, 95; 623/11, 1, 13, 23.48; 600/37

(56) References Cited

U.S. PATENT DOCUMENTS

| | | | | |
|---|---|---|---|---|
| 2,667,117 A | * | 1/1954 | Millard et al. | 99/418 |
| 4,138,939 A | * | 2/1979 | Feld | 99/418 |
| 4,276,659 A | * | 7/1981 | Hardinge | 3/1.9 |
| 4,769,038 A | * | 9/1988 | Bendavid et al. | 623/13 |
| D316,505 S | * | 4/1991 | Chow | D7/667 |
| 5,147,374 A | * | 9/1992 | Fernandez | 606/151 |
| 5,192,301 A | * | 3/1993 | Kamiya et al. | 606/213 |
| 5,356,432 A | | 10/1994 | Rutkow et al. | |
| 5,716,408 A | | 2/1998 | Eldridge et al. | |
| 5,741,297 A | | 4/1998 | Simon | |
| 6,066,776 A | | 5/2000 | Goodwin et al. | |
| 6,090,996 A | * | 7/2000 | Li | 623/11 |
| 6,166,286 A | | 12/2000 | Trabucco | |
| 6,180,848 B1 | * | 1/2001 | Flament et al. | 623/11 |

FOREIGN PATENT DOCUMENTS

| | | |
|---|---|---|
| EP | 0614650 | 9/1994 |
| WO | 9745068 | 12/1997 |
| WO | 9903422 | 1/1999 |

* cited by examiner

Primary Examiner—John J. Calvert
Assistant Examiner—Alissa L. Hoey

(57) ABSTRACT

A prosthesis for repairing a tissue or muscle wall defect includes a plurality of petals connected to one another at a common center. The petals are arranged in circular fashion and cooperate to form a substantially flat disc. The petals are also arranged in an overlapping manner such that each of the petals is movable relative to an adjacent pair of the petals. The petals are sized and shaped such that at least some of the petals come in direct contact with a surrounding structure of a tissue defect when the prosthesis is inserted therein.

13 Claims, 4 Drawing Sheets

HERNIA REPAIR DEVICE

FIELD OF THE INVENTION

The present invention relates to a device for repairing a hernia defect, and more particularly, to a space-filling plug device for repairing a hernia defect.

BACKGROUND OF THE INVENTION

In the past, plug-type devices have been used for repairing hernia defects (e.g., openings or holes formed in a wall of an organ, through which interior organs tend to protrude). For instance, U.S. Pat. No. 6,066,776 discloses a plug-type prosthesis having multiple layers of meshes stacked one on top of another. In order to repair hernia defects, the prosthesis is pushed into an opening of a hernia defect. During the implantation process, wrinkles tend to form in or between the layers of the prosthesis. As a result, organic materials may flow through or between these wrinkles, and impede healing and/or cause recurrence of hernia.

U.S. Pat. Nos. 5,356,432 and 5,716,408 disclose prostheses for hernia repair. More particularly, the prostheses have outer conical bodies for allowing same to conform to irregularities in tissue or muscle walls defining hernia defects. The outer bodies have pre-formed pleats. Due to the construction of these pleats, it is difficult to manufacture the prostheses, hence increasing production costs. Further, non-uniform forces could be applied to tissue or muscle walls around hernia defects during an implanting process.

In the foregoing circumstances, there is a need for a device adapted for use in repairing hernia defects without the problems and/or shortcomings described above.

SUMMARY OF THE INVENTION

The present invention overcomes the disadvantages and shortcomings of the prior art discussed above by providing a new and improved prosthesis for repairing a tissue or muscle wall defect. More particularly, the prosthesis includes a plurality of petals connected to one another at a common center. The petals are arranged in circular fashion so as to form a substantially flat disc. The petals are also arranged in an overlapping manner such that each of the petals is movable relative to an adjacent pair of the petals. The petals are sized and shaped such that at least some of the petals come in direct contact with a surrounding structure of a tissue defect when the prosthesis is inserted therein. In accordance with one feature of the present invention, the prosthesis can be used as a space-filling plug or as a patch for hernia repair.

BRIEF DESCRIPTION OF THE DRAWINGS

For a more complete understanding of the present invention, reference is made to the following detailed description of exemplary embodiments considered in conjunction with the accompanying drawings, in which.

DETAILED DESCRIPTION OF THE EXEMPLARY EMBODIMENTS

Figure 1:
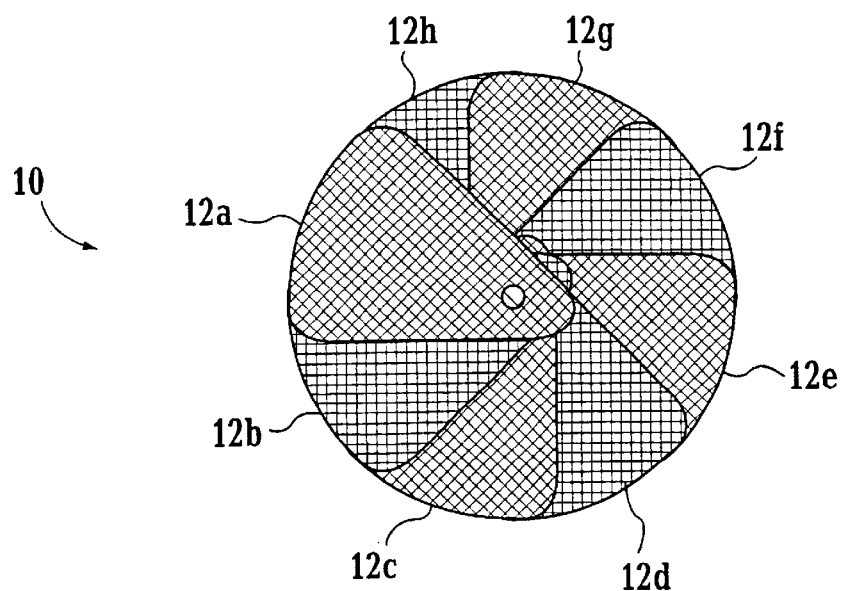
FIG. 1 is a plan view of a hernia repair device constructed in accordance with a first embodiment of the present invention.
Figure 2:
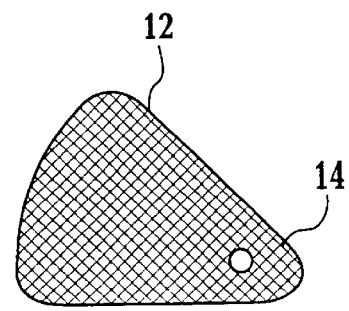
FIG. 2 is a plan view of a petal used in the device shown in FIG. 1.

FIG. 1 shows a hernia repairing device 10 constructed in accordance with a first embodiment of the present invention. More particularly, the device 10 includes a plurality of petals 12a–12h, each of which has a sector shape and a connecting end 14 (see FIG. 2). The petals 12a–12h are arranged in a spirally overlapping manner. That is, the petal 12a at least partially overlaps the petal 12b, which in turn partially overlaps the petal 12c. Likewise, the petal 12d at least partially overlaps the petal 12e, which partially overlaps the petal 12f. The remaining petals 12f–12h overlap an adjacent petal in similar fashion. While any degree of overlapping can be used in connection with the present invention, an angular displacement (i.e., an angle at which adjacent petals are oriented with respect to one another) of about 45° is particularly suitable. The petals 12a–12h are attached (e.g., stitched or welded) to one another at their connecting ends 14 (i.e., at a common center) so as to retain their spirally overlapping design. In this manner, the petals 12a–12h cooperate to form a generally flat (i.e., planar) disc having a substantially "continuous" surface. Because of their spirally overlapping design, the petals 12a–12h are movable relative to one another.

The petals 12a–12h can be made from any conventional materials used in the medical field for making hernia repair devices. For instance, the petals 12a–12h can be made from a biocompatible, flexible mesh fabric, such as a polypropylene mesh. Other materials, such as polytetraflouroethylene, can also be used for making the device 10.

Figure 3:
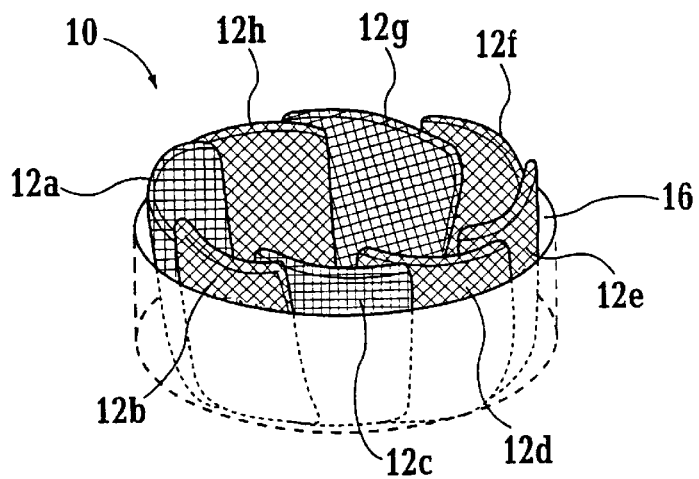
FIG. 3 is a schematic view of the device shown in FIG. 1, the device being placed in a hernia defect.

With reference to FIG. 3, the device 10 can be used as a plug like the devices shown in U.S. Pat. Nos. 5,356,432, 5,716,408 and 6,066,776. When used as a plug, the device 10 is inserted or pressed in a conventional manner into an opening or hole 16 (i.e., a hernia defect) developed in a wall of an organ. When the device 10 is inserted into the opening 16, the petals 12a–12h bypass each other in overlapping fashion so as to shape the flat device 10 into a three-dimensional plug which conforms substantially to the anatomy (e.g., the shape) of the opening 16. That is, the petals 12a–12h directly come in contact with a tissue surrounding the opening 16. After properly placing the device 10 in the opening 16, each of the petals 12a–12h can be sutured to the periphery of the opening 16. If desired, an onlay patch (not shown) can be applied separately or as part of the device 10 to further secure the device 10 in its proper position.

It should be appreciated that the device 10 provides numerous advantages over the prior art discussed above. For instance, because of their spiral, overlapping design, the petals 12a–12h automatically conform to the shape of a hernia defect and form a three-dimensional plug in vivo without forming pleats or being wrinkled. In such circumstances, the petals 12a–12h provide an enhanced plugging function compared with the prior art, thereby promoting healing and/or inhibiting hernia recurrence.

Figure 4:
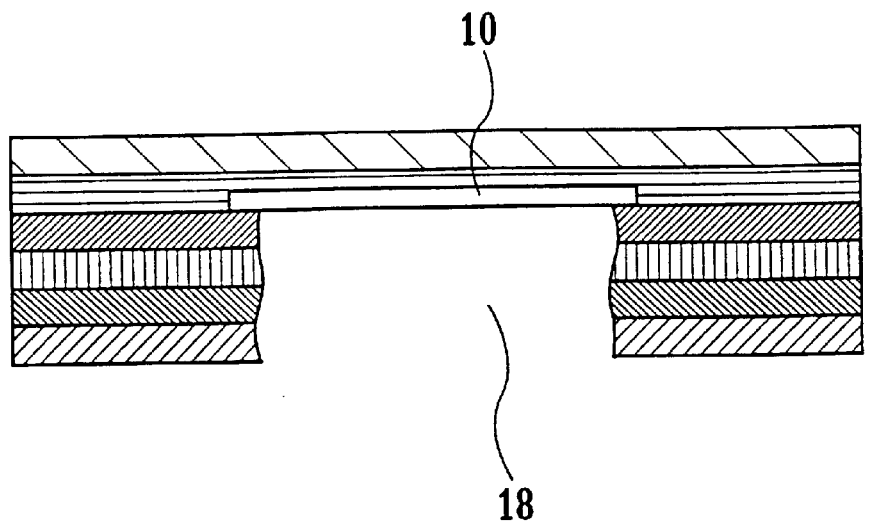
FIG. 4 is a schematic view of the device shown in FIG. 1 in a different application.
Figure 5:
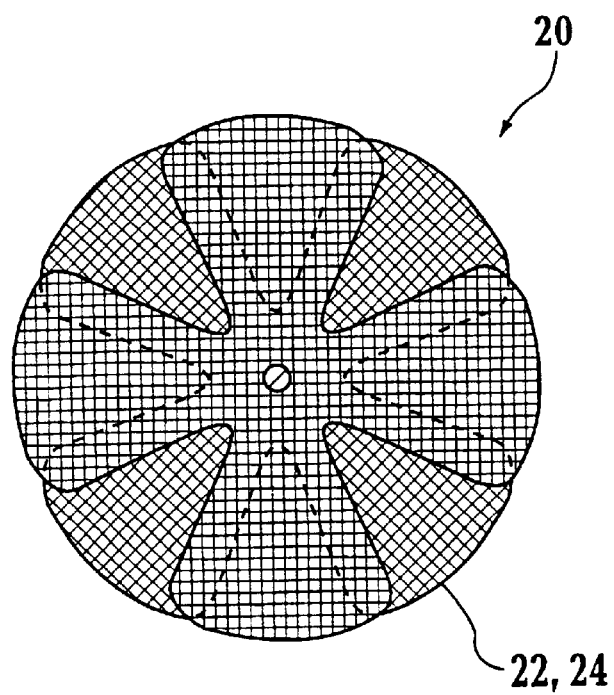
FIG. 5 is a plan view of a hernia repair device constructed in accordance with a second embodiment of the present invention.

It has been found, surprisingly and unexpectedly, that the device 10 can also be used as a patch for repairing hernia defects (see FIG. 4). More particularly, because the petals 12a–12h can be placed into a hernia defect without the formation of wrinkles, even if the petals are "folded" during an implanting process, they can readily be unfolded back to their flat shape. In such circumstances, the device 10 can be inserted into an opening of a hernia defect 18 for use as patch for repairing the defect.

It should be noted that the device 10 can have numerous modifications and variations. For instance, the device 10 can be provided with any sizes (e.g., diameters) used for conventional hernia repair devices. For instance, such sizes are typically determined by the specific applications and/or requirements associated with hernia repair devices. While the device 10 is shown in FIG. 1 as having eight petals with about a 45° offset angle, it can be provided with a different number of petals, as well as with a different offset angle. Moreover, the flat disc shape of the device 10 can include numerous geometrical (e.g., circular, oval, etc.) shapes.

Figure 6:
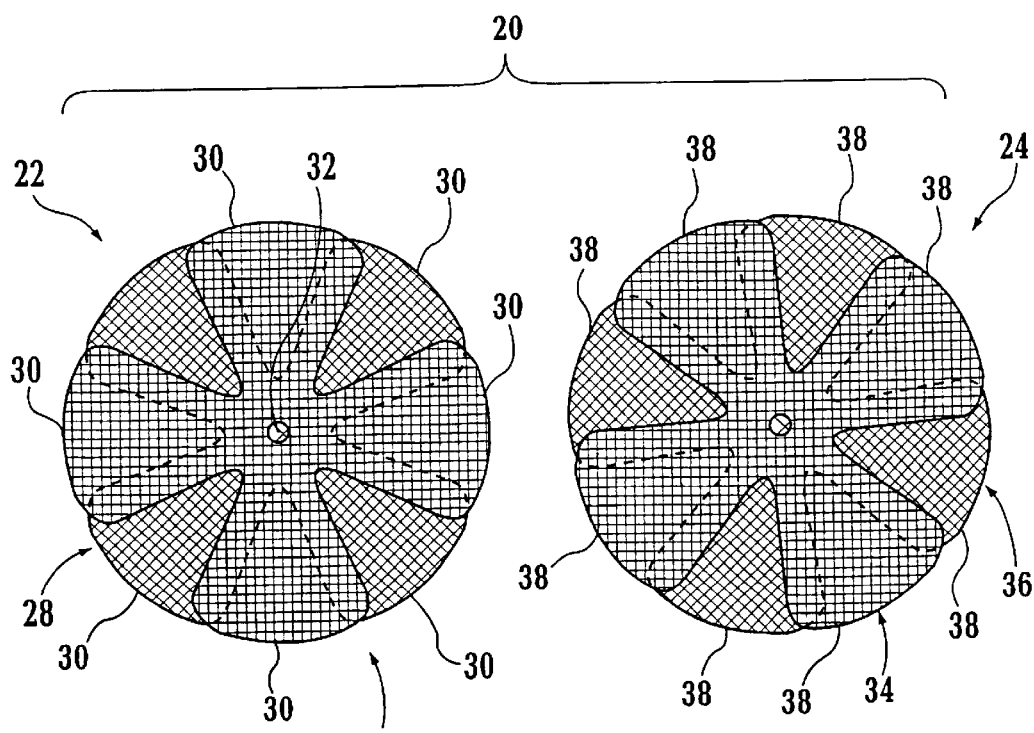
FIG. 6 is a plan view of subassemblies of the device shown in FIG. 5.
Figure 7:
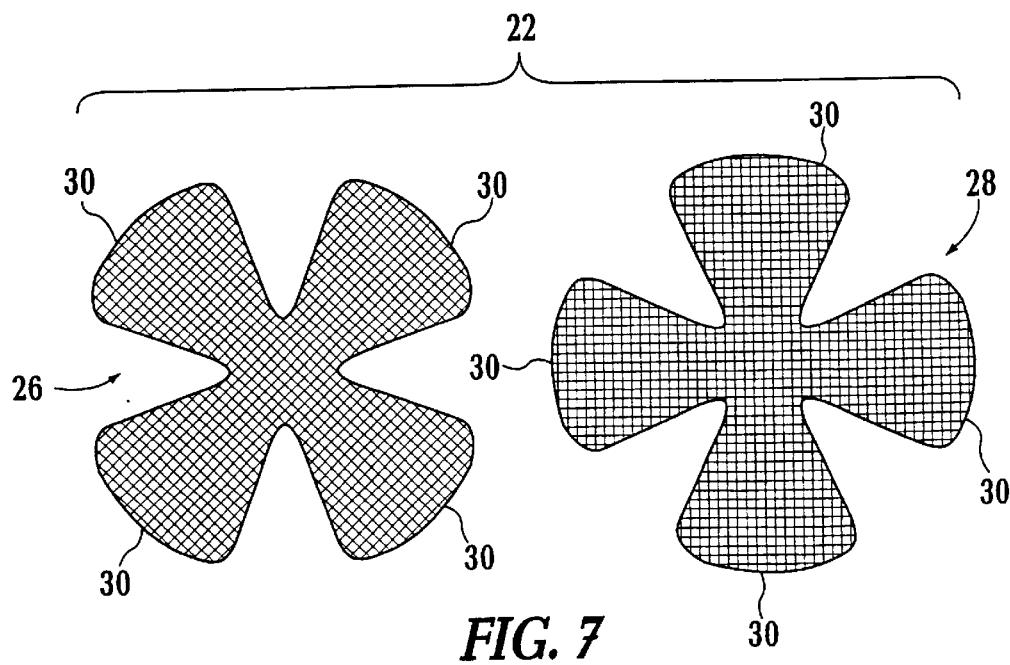
FIG. 7 is a plan view of layers of one of the subassemblies shown in FIG. 6.
Figure 8:
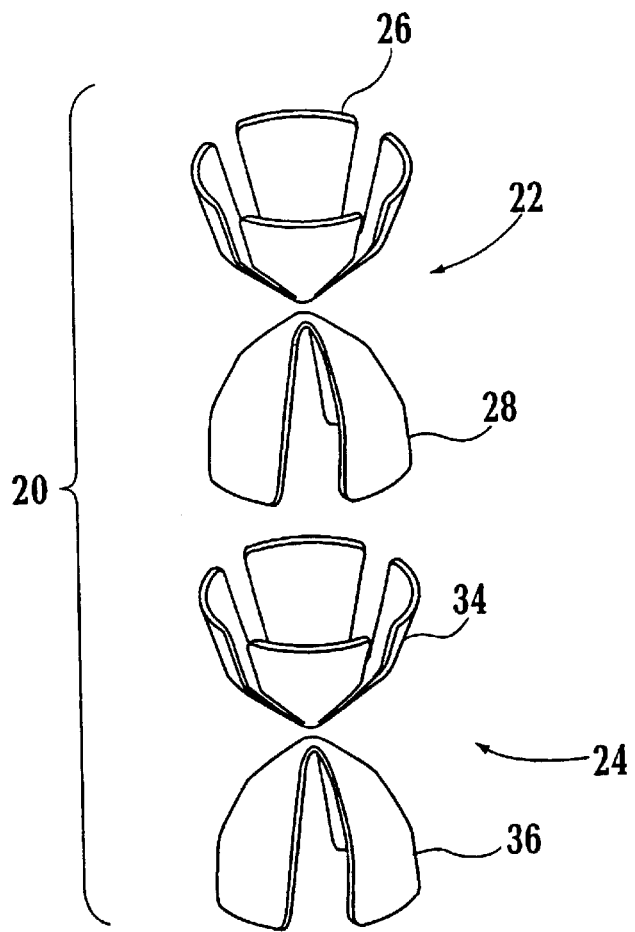
FIG. 8 is an exploded view of the device shown in FIG. 5.

FIGS. 5–9 illustrate a hernia repair device 20 constructed in accordance with a second embodiment of the present invention. More particularly, the device 20 includes a pair of subassemblies 22, 24 (see FIG. 6) having a construction identical to one another. The subassembly 22 has a pair of clover leaf-shaped layers 26, 28, each of which includes a plurality of leaves 30 (i.e., petals) projecting radially outwardly from a common center 32 and spaced from an adjacent pair of the leaves 30 (see FIGS. 6 and 7). That is, the leaves 30 have ends which are integrally formed with each other. The layers 26, 28 are thermoformed so as to provide same with a slight conical shape, as shown in FIG. 8. As a result, each of the leaves 30 has a curved shape. The layers 26, 28 are bonded (e.g., welded or stitched) to one another at the center 32 and are oriented at a predetermined angle (e.g., about a 45° angle) with respect to each other such that the leaves 30 of the layer 26 are arranged in an overlapping manner with respect to the leaves 30 of the layer 28 (see FIG. 6).

As mentioned above, the subassembly 24 has a construction identical to that of the subassembly 22. For instance, the subassembly 24 has a pair of clover leaf-shaped layers 34, 36, each of which has a plurality of leaves 38. In the foregoing circumstances, a detailed discussion of the construction of the subassembly 24 will not be provided herein.

Referring to FIGS. 6 and 7, the subassemblies 22, 24 are bonded (e.g., stitched or welded) to each other at the center 32. More particularly, the subassemblies 22, 24 are arranged relative to one another at a predetermined angle (e.g., about a 22.5° angle), providing the device 20 with a substantially flat circular shape (see FIG. 5).

Figure 9:
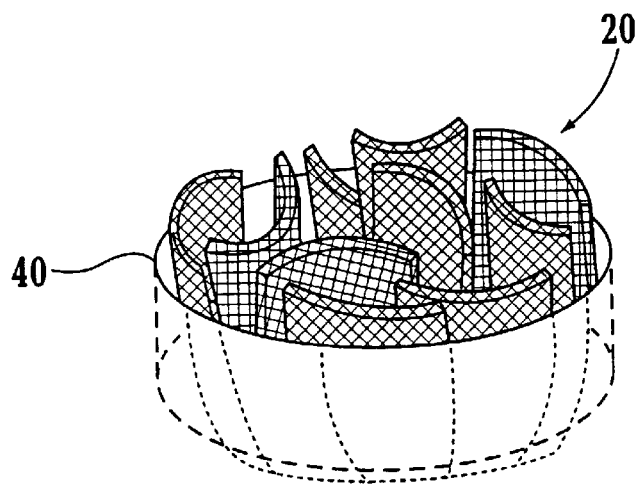
FIG. 9 is a schematic view of the device shown in FIG. 5, the device being placed in a hernia defect.

With reference to FIG. 9, the device 20 is usable as a plug for repairing a hernia defect 40. More particularly, when inserted into the hernia defect 40 in a conventional manner, the leaves 30, 38 of the device 20 curve or fold upwardly toward the center axis of the device 20. When properly placed in the defect 40, at least some of the leaves 30, 38 fill in the center of the folded device 20 and create and/or maintain a radial expansion force against walls of the defect 40, while at least some of the leaves 30, 38 come in direct contact with the walls. The leaves 30, 38 of the device 20 are then sutured to the walls of the defect 40. Alternatively, an onlay patch (not shown) can be applied to secure the device 20 in its proper position.

It should be noted that the device 20 can have numerous modifications and variations. For instance, the subassembly 22 and the subassembly 24 can be used individually and separately without the other subassembly in the same basic manner as the device of FIGS. 1–4 (i.e., either as a plug or a patch). Moreover, the layers 26, 28, 34, 36 can be provided with a different shape. Further, additional layers of leaves can be utilized in the device 20.

It will be understood that the embodiments described herein are merely exemplary and that a person skilled in the art may make many variations and modifications, including those discussed above, without departing from the spirit and scope of the invention. All such variations and modifications are intended to be included within the scope of the invention as defined in the appended claims.

I claim:

1. A prosthesis for repairing a tissue or muscle wall defect, comprising a plurality of discrete petals attached to one another at a common center, said petals being arranged in circular fashion and cooperating so as to form a substantially flat disc, said petals being arranged in an overlapping manner such that each of said petals is movable relative to an adjacent pair of said petals, said petals being sized and shaped such that at least some of said petals come in direct contact with a surrounding structure of a tissue defect when said disc is inserted therein, each of said petals having a sector shape and an end, and said ends of said petals being attached to each other.

2. The prosthesis of claim 1, wherein said petals are sized and shaped such that said disc is usable as a plug or as a patch for repairing a tissue defect.

3. The prosthesis of claim 1, wherein said disc has a circular shape.

4. A prosthesis for repairing a tissue or muscle wall defect, comprising a plurality of petals connected to one another at a common center, said petals being arranged in circular fashion and cooperating so as to form a substantially flat disc, each of said petals being overlapped with an adjacent pair of said petals so as to be movable relative thereto, said petals being sized and shaped such that at least some of said petals come in direct contact with a surrounding structure of a tissue defect when said disc is inserted therein, said petals being discrete members attached to one another at said common center, each of said petals having a sector shape and an end, and said ends of said petals being attached to each other.

5. The prosthesis of claim 4, wherein said petals are arranged in a spirally overlapping manner such that when said disc is inserted into a tissue defect, said petals forms a three-dimensional plug.

6. The prosthesis of claim 4, wherein said petals are arranged in a spirally overlapping manner such that when said disc is inserted into a tissue defect, said petals can be unfolded so as to form a patch for repairing the tissue defect.

7. A prosthesis for repairing a tissue or muscle wall defect, comprising a plurality of petals connected to one another at a common center, said petals being arranged in circular fashion and cooperating so as to form a substantially flat disc, each of said petals being overlapped with an adjacent pair of said petals so as to be movable relative thereto, said petals being sized and shaped such that at least some of said petals come in direct contact with a surrounding structure of a tissue defect when said disc is inserted therein, at least one set of said petals being formed integrally so as to form a first layer, at least another set of said petals being formed integrally so as to form a second layer, said first and second layers cooperating to define said disc, said first layer being laid on and attached to said second layer, said first layer and said second layer being oriented such that each of said petals of said first layer overlaps with an adjacent pair of said petals of said second layer, and said first and second layers forming a subassembly of petals.

8. The prosthesis of claim 7, wherein at least some of said petals are formed integrally so as to form a third layer; and wherein at least some of said petals are formed integrally so as to form a fourth layer.

9. The prosthesis of claim 8, wherein said third layer is laid on and attached to said fourth layer.

10. The prosthesis of claim 9, wherein said third layer and said fourth layer are oriented such that each of said petals of said third layer overlaps with an adjacent pair of said petals of said fourth layer.

11. The prosthesis of claim 10, wherein said third and fourth layers form another subassembly of petals.

12. The prosthesis of claim 11, wherein said subassembly is laid on said another subassembly, said subassembly and said another subassembly being attached to one another at said common center so as to define said disc.

13. The prosthesis of claim 12, wherein each of said first, second, third and fourth layers has a clover leaf shape.

* * * * *